United States Patent [19]

Small et al.

[11] Patent Number: 5,773,615
[45] Date of Patent: Jun. 30, 1998

[54] INTERMITTENT ELECTROLYTIC PACKED BED SUPPRESSOR REGENERATION FOR ION CHROMATOGRAPHY

[75] Inventors: Hamish Small, Leland, Mich.; John M. Riviello, Santa Cruz; Steven B. Rabin, Mountain View, both of Calif.

[73] Assignee: Dionex Corporation, Sunnyvale, Calif.

[21] Appl. No.: 600,856

[22] Filed: Feb. 13, 1996

Related U.S. Application Data

[63] Continuation of Ser. No. 397,998, Mar. 3, 1995, Pat. No. 5,633,171.
[51] Int. Cl.$^6$ .................................................. G01N 30/02
[52] U.S. Cl. ..................... 436/161; 73/61.53; 210/198.2; 210/656; 422/70; 422/82.02; 436/149; 436/175
[58] Field of Search ...................................... 736/161, 149, 736/175; 422/82.02, 70; 210/635, 656, 198.2, 670; 73/61.52, 61.53, 61.55, 61.58; 204/130, 131, 187.4, 272

[56] References Cited

U.S. PATENT DOCUMENTS

| | | | |
|---|---|---|---|
| 2,980,598 | 4/1961 | Stoddard | 204/151 |
| 3,920,397 | 11/1975 | Small et al. | 436/79 |
| 5,423,965 | 6/1995 | Kunz | 204/182.4 |

OTHER PUBLICATIONS

Rabin et al., J. Chromatography vol. 640 pp. 97–109 (1993).

*Primary Examiner*—Jan Ludlow
*Attorney, Agent, or Firm*—David J. Brezner, Esq.

[57] ABSTRACT

Method and apparatus for ion chromatography including passage of sample through a chromatographic separation column, through a suppressor column containing a resin with exchangeable ions, and then through a detector. The suppressor column is equipped with an electrical potential supplying device to electrolyze water and regenerate the suppressor column.

11 Claims, 8 Drawing Sheets

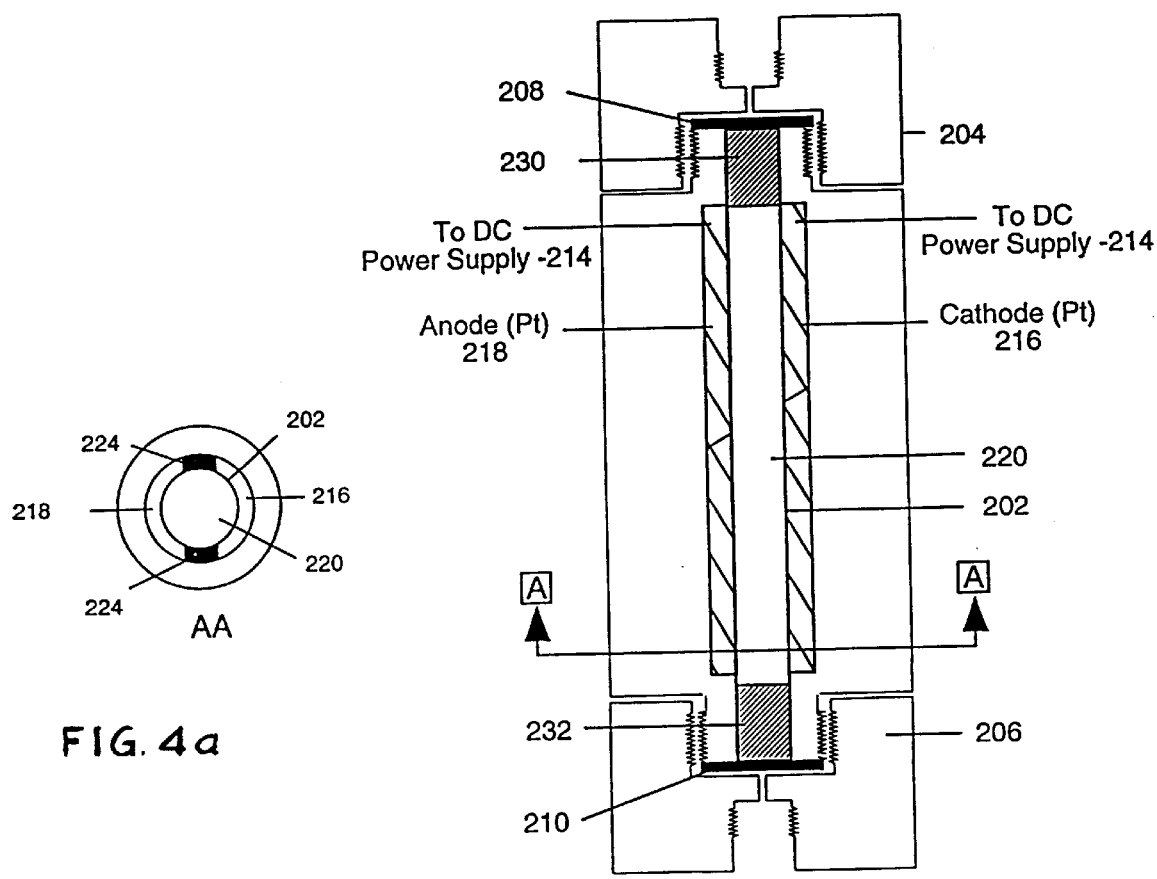

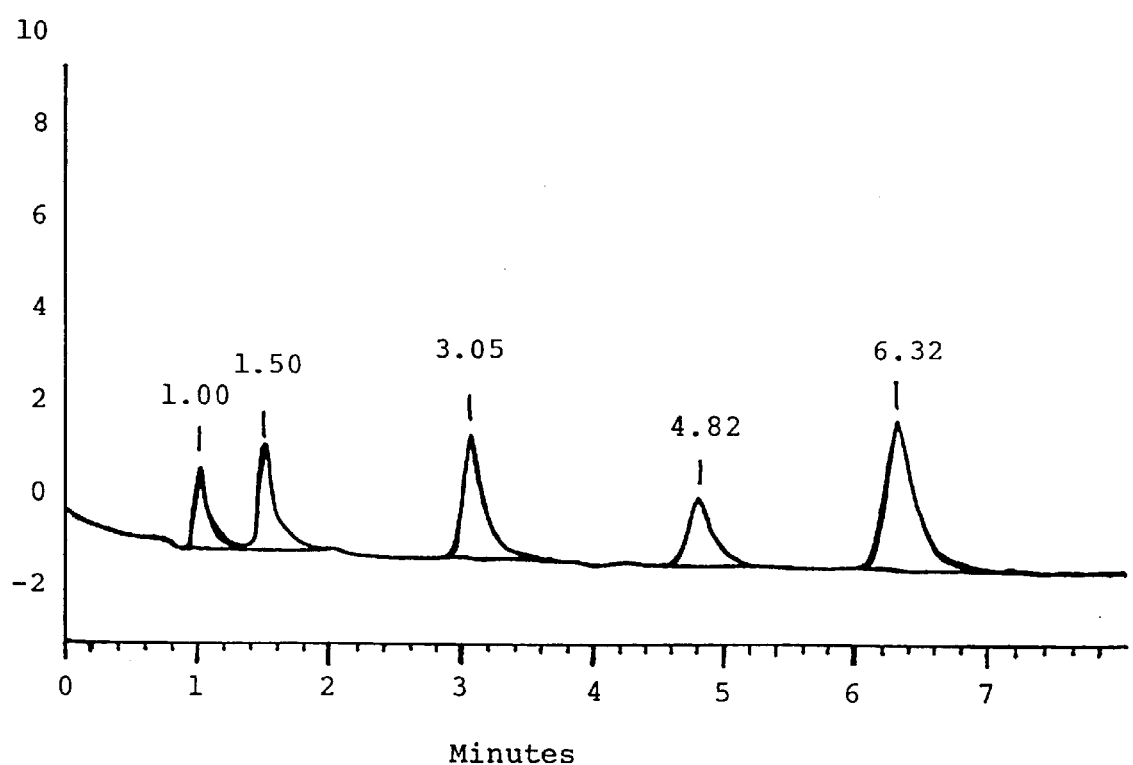

INTERMITTENT ELECTROLYTIC PACKED BED SUPPRESSOR REGENERATION FOR ION CHROMATOGRAPHY

This is a continuation of application Ser. No. 08/397,998 filed Mar. 3, 1995, now U.S. Pat. No. 5,633,171.

BACKGROUND OF THE INVENTION

The present invention relates to method and apparatus using suppression of eluents for the analysis of anions or cations in ion chromatography.

Ion chromatography is a known technique for the analysis of ions which typically includes a chromatographic separation stage using an eluent containing an electrolyte, and an eluent suppression stage, followed by detection, typically by an electrical conductivity detector. In the chromatographic separation stage, ions of an injected sample are eluted through a separation column using an electrolyte as the eluent. In the suppression stage, electrical conductivity of the electrolyte is suppressed but not that of the separated ions so that the latter may be determined by a conductivity cell. This technique is described in detail in U.S. Pat. Nos. 3,897,213, 3,920,397, 3,925,019 and 3,926,559.

Suppression or stripping of the electrolyte is described in the above prior art references by an ion exchange resin bed commonly referred to as a packed bed suppressor (PBS). The PBS requires periodic regeneration by flushing with an acid or base solution.

While packed bed suppressors have proven useful in ion chromatography, there are a number of disadvantages of PBS. These disadvantages include a) periodic regeneration of the PBS which interrupts sample analysis, b) a loss of resolution due to band broadening in the PBS and c) changes in retention of certain analytes as a function of the degree of exhaustion of the PBS.

The volume of the PBS suppressors is generally large as to contain sufficient ion exchange resin so that the suppression reaction can be performed for a large number of analysis (e.g. 15 to 50) prior to regeneration. By making the volume and capacity of the suppressor sufficiently large, the need to regenerate is less frequent which permits a larger number of samples to be analyzed before the system must be disrupted to regenerate the suppressor. Regeneration typically requires placing the suppressor out of line of the analytical system and pumping a concentrated acid or base solution (regenerant) through the suppressor.

If the suppressor's volume is too large, the separation of the analytes achieved in the separator column is compromised due to re-mixing of the analytes in the void volume, resulting in lower resolution.. Thus, the suppressor volume is a compromise between regeneration frequency and chromatographic resolution.

The regeneration process typically requires 20–60 minutes, depending on the volume of the suppressor. A strong acid or base solution is first pumped through the PBS in order to convert the resin to the acid ($H_3O^+$) or base ($OH^-$) form. After this conversion, deionized water is pumped through the suppressor until any traces of the highly conductive acid or base regenerant have been removed. The PBS is then placed back in line with the analytical system and is allowed to equilibrate before sample analysis is performed.

A different form of a suppressor is described and published in U.S. Pat No. 4,474,664, in which a charged ion exchange membrane in the form of a fiber or sheet is used in place of the resin bed. The sample and eluent are passed on one side of the membrane with a flowing regenerant on the other side, the membrane partitioning the regenerant from the effluent of the chromatographic separation. The membrane passes ions of the same charge as the exchangeable ions of the membrane to convert the electrolyte of the eluent to weakly ionized form, followed by detection of the ions.

Another suppression system is disclosed in U.S. Pat. No. 4,459,357. There, the effluent from a chromatographic column is passed through an open flow channel defined by flat membranes on both sides of the channel. On the opposite sides of both membranes are open channels through which regenerant solution is passed. As with the fiber suppressor, the flat membranes pass ions of the same charge as the exchangeable ions of the membrane. An electric field is passed between electrodes on opposite sides of the effluent channel to increase the mobility of the ion exchange. One problem with this electrodialytic membrane suppressor system is that very high voltages (50–500 volts DC) are required. As the liquid stream becomes deionized, electrical resistance increases, resulting in substantial heat production. Such heat is detrimental to effective detection because it greatly increases noise and decreases sensitivity.

In U.S. Pat. No. 4,403,039, another form of electrodialytic suppressor is disclosed in which the ion exchange membranes are in the form of concentric tubes. One of the electrodes is at the center of the innermost tube. One problem with this form of suppressor is limited exchange capacity. Although the electrical field enhances ion mobility, the device is still dependent on diffusion of ions in the bulk solution to the membrane.

Another form of suppressor is described in U.S. Pat. No. 4,999,098. In this apparatus, the suppressor includes at least one regenerant compartment and one chromatographic effluent compartment separated by an ion exchange membrane sheet. The sheet allows transmembrane passage of ions of the same charge as its exchangeable ions. Ion exchange screens are used in the regenerant and effluent compartments. Flow from the effluent compartment is directed to a detector, such as an electrical conductivity detector, for detecting the resolved ionic species. The screens provide ion exchange sites and serve to provide site to site transfer paths across the effluent flow channel so that suppression capacity is no longer limited by diffusion of ions in the bulk solution to the membrane. A sandwich suppressor is also disclosed including a second membrane sheet opposite to the first membrane sheet and defining a second regenerant compartment. Spaced electrodes are disclosed in communication with both regenerant chambers along the length of the suppressor. By applying an electrical potential across the electrodes, there is an increase in the suppression capacity of the device. The patent discloses a typical regenerant solution (acid or base) flowing in the regenerant flow channels and supplied from a regenerant delivery source. In a typical anion analysis system, sodium hydroxide is the electrolyte developing reagent and sulfuric acid is the regenerant. The patent also discloses the possibility of using water to replace the regenerant solution in the electrodialytic mode.

Another improvement in suppression is described in U.S. Pat. No. 5,248,426. This form of suppressor was introduced in 1992 by Dionex Corporation under the name "Self Regenerating Suppressor" (SRS). A direct current power controller generates an electric field across two platinum electrodes to electrolyze water in the regenerant channels. Functionalized ion-exchange screens are present in the regenerant chambers to facilitate electric current passage with permselective ion-exchange membrane defining the chromatography eluent chamber, as in the '098 patent. After detection, the chromatography effluent is recycled through the suppressor to form a flowing sump for electrolyte ion as well as providing the water for the electrolysis generating acid or base for suppression.

The history of ion chromatography suppression is summarized in Rabin, S. et al. *J. of Chromatog.* 640 (1993) 97–109, incorporated herein by reference.

SUMMARY OF THE INVENTION

The present invention relates to ion chromatography using electrochemical regeneration of a packed bed suppressor. Method and apparatus are provided using electrolytic chemical regeneration of a packed bed suppressor containing ion exchange resin. Ion chromatography is performed in a conventional manner by chromatographic separation, chemical suppression in a packed bed and detection. Thereafter, and before a second run, an electrical potential is passed through the packed bed suppressor while flowing an aqueous stream through it to electrolyze water in the stream and thereby create hydronium or hydroxide ions to regenerate the ion exchange resin. The packed bed suppressor with capacity sufficient for several analyses, has electrodes embedded in the resin, which permits electrochemical regeneration. Electrochemical regeneration is performed after one analysis, or after many analyses, depending on the capacity of the packed bed suppressor. In one embodiment, the aqueous liquid stream is the eluent. In another embodiment, the aqueous liquid stream is an independent water source, preferably deionized water. In that instance, appropriate valving is provided so that after a run, the deionized water is passed through the bed and electrolyte bypasses the bed, while the electrical potential is being applied to regenerate the resin.

In a further embodiment, a second ion exchange resin bed is used with suitable valving to pass liquid streams through the system. In one alternative of this system, a second sample in an eluent stream is chromatographically separated, typically on a chromatographic column using an eluent. The eluent and separated second sample flow through a second packed bed suppressor including ion exchange resin to convert the electrolyte to weakly ionized form. Then, the separated sample ionic species in the suppressor effluent are detected in the detector. The effluent then flows through the first packed bed suppressor, forming the aqueous liquid stream required for regeneration and an electrical potential is applied and regeneration of the first packed bed suppressor is accomplished. The second suppressor may be similarly regenerated by positioning it after the detection cell and flowing through the detector effluent of the first sample and applying an electrical potential.

In another embodiment, the second suppressor is used solely as a flow-through polishing unit, not as a suppressor prior to detection. Instead, an eluent solution containing electrolyte flows through the polishing unit to convert the electrolyte into weakly ionized form and form a polished liquid effluent which flows through the first packed bed suppressor to supply the water source for electrolysis. The polishing unit is regenerated electrolyzing a stream of the first sample effluent from the detector.

Apparatus is provided to perform the above packed bed suppressor methods. Such apparatus includes a suppressor with an ion exchange resin bed and means for applying an electrical potential to electrolyze water in a flowing stream and regenerate suppressor ion exchange resin after use to suppress the electrolyte in the eluent stream.

One apparatus uses two packed bed suppressors with appropriate valving. In one valving embodiment, in a first valve position, a first sample is suppressed on a first suppressor and flows through the detector forming an aqueous liquid stream for regenerating the second suppressor while applying an electric field. In the second position, the flow is reversed as are the functions of the two suppressors. The electrical potential is applied only to that suppressor which is not in the flow system upstream of the detector.

In the polishing system, only one ion exchange packed bed is used as a suppressor while the other one is dedicated to providing a polished liquid for regeneration of the suppressor. The valving is substantially the same as the two-suppressor system.

BRIEF DESCRIPTION OF THE DRAWINGS

FIGS. 4 and 4a are side view, partial cross-section and a cross-sectional view along the line A—A, of another electrolytic chemical packed bed suppressor.

FIGS. 7 and 8 are chromatograms illustrating the present invention.

DETAILED DESCRIPTION OF THE PREFERRED EMBODIMENTS

The system of the present invention is useful for determining a large number of ionic species so long as the species to be determined are solely anions or solely cations. A suitable sample includes surface waters, and other liquids such as industrial chemical wastes, body fluids, beverages such as fruits and wines and drinking water. When the term "ionic species" is used herein, it includes species in ionic form and components of molecules which are ionizable under the conditions of the present system.

The purpose of the suppressor stage is to reduce the conductivity, and hence noise, of the analysis stream background while enhancing the conductivity of the analytes (i.e., increasing the signal/noise ratio), while maintaining chromatographic efficiency. Thus, the following parameters are important to the performance of the suppressor: (1) capacity of the suppressor, measured as $\mu Eq/mL$ of the suppressor resin; (2) the volume of the suppressor; (3) the ratio of the i.d. to the length of the suppressor; and (4) background conductivity measured as $\mu S/cm$ for each device.

The present invention relates to the intermittent use of the electric field during electrochemical suppression to minimize noise during detection of the ionic species. Specifically, it has been found that the suppressor can be regenerated to a sufficient extent to convert the chromatography electrolyte to a weakly dissociated form so that detection can be performed in the absence of the electric field. When used in this configuration, the requirement for chemical regenerants is eliminated, the assembly does not require the use of a membrane to provide uninterrupted use, the absence of a membrane allows a higher tolerance to system backpressure and reduces manufacturing costs, and, finally, this configuration reduces system noise because of the absence of an applied electrical field during detection. As used herein, the term intermittent electrochemical suppression will refer to this type of system.

It is preferable for electrolytic chemical packed bed regeneration to provide direct contact of the electrodes with the ion exchange resin bed itself. For anion analysis using sodium hydroxide eluent, the cation exchange resin bed is regenerated to the hydronium ion form by formation of hydronium ions at the anode, which migrate toward the cathode, displacing sodium ions from the ion exchange sites. Sodium ions associate with hydroxide ions generated at the cathode and are eluted from the suppressor as sodium hydroxide. Current is conducted between the electrodes by movement of ions along ion exchange sites in the ion exchange material in the bed. After regeneration, the current is discontinued, and eluent is pumped through the bed to remove remaining gas bubbles. Then, the ionic species in a new sample solution are separated in the chromatography column, flow through the suppressor, and are detected.

Figure 1:
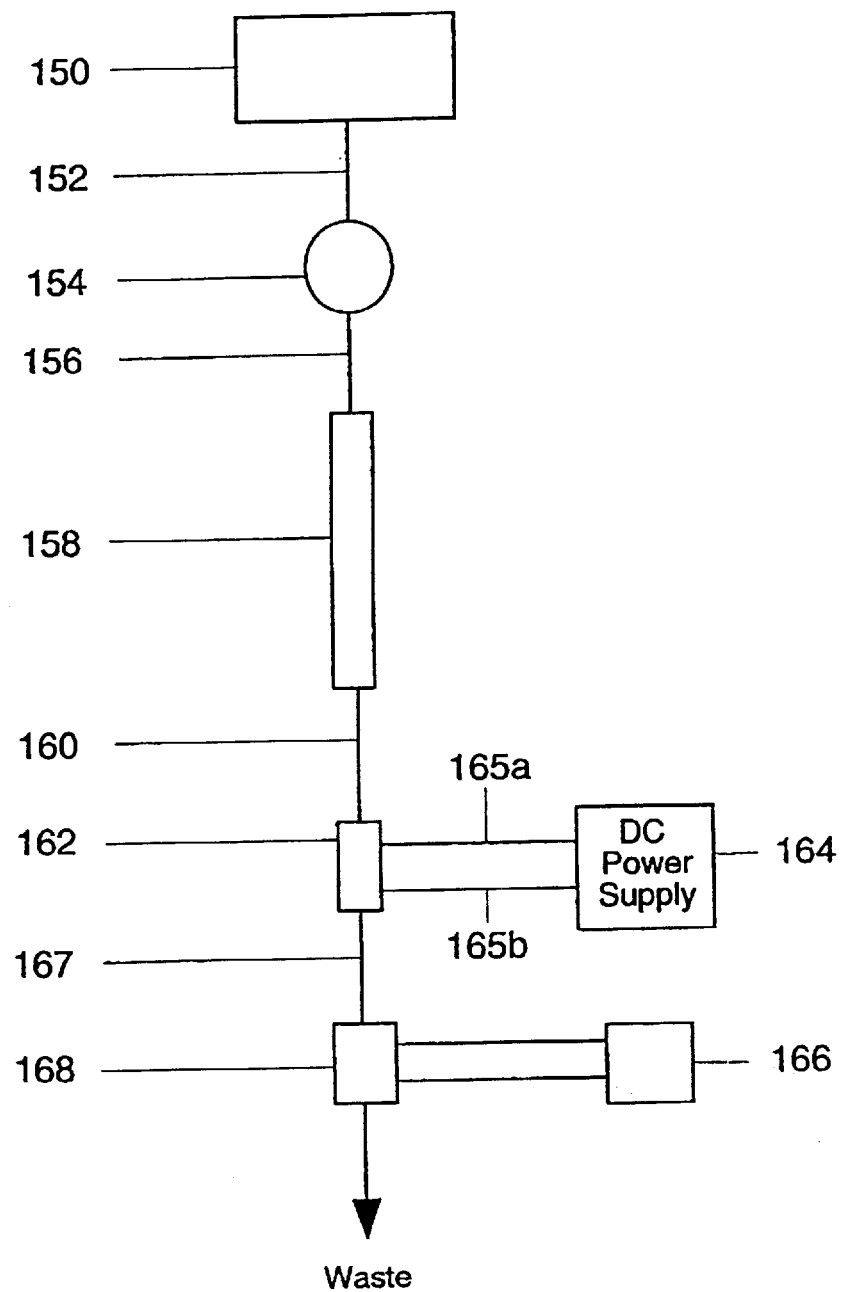
FIGS. 1 and 2 are schematic views of two different systems according to the present invention using a single packed bed electrolytic chemical suppressor.

Referring to FIG. 1, one form of an ion chromatography system is illustrated using a single packed bed suppressor. The system includes analytical pump 150 connected by tubing 152 to sample injection valve 154 which in turn is connected by tubing 156 to chromatographic means typically in the form of a chromatographic column 158 filled with chromatographic resin. The effluent from chromatographic column 158 flows through tubing 160 to a packed ion exchange resin bed suppressor 162. Electrodes, in a form to be described below, are spaced apart in the suppressor with the ion exchange resin disposed between them. The electrodes are connected to a direct current power supply 164 by leads 165a and 165b. The configuration is such that with an aqueous stream in the suppressor and the application of power, water in the aqueous stream is electrolyzed to form a source of hydronium ion or hydroxide ion to regenerate the ion exchange resin. The suppressor effluent is directed through tubing 167 to a suitable detector and then to waste. A preferred detector is a conductivity detector 166 with the chromatography effluent flowing through the conductivity cell 168 of detector 166.

The suppressor 162 generates hydronium ions (and oxygen gas) at the anode (positive) electrode and hydroxide ions (and hydrogen gas) at the cathode (negative) electrode. In the first stage of operation, the power supply 164 is turned off. Thus, the system operates in the manner of a standard ion chromatography system. That is, a water-containing eluent solution including electrolyte is directed from pump 150 and through tubing 152. Sample is injected through sample injection valve 154, and is directed by tubing 156 into chromatographic column 158 to form a first chromatography effluent including separated ionic species of the sample.

For simplicity of description, the system will be described with respect to the analysis of anions using an eluent solution including sodium hydroxide as the electrolyte.

The chromatography effluent is directed in tubing 160 to suppressor 162. The suppressor includes cation exchange resin with exchangeable hydronium ions. The sodium ions of the electrolyte displace the hydronium ions on the column. The displaced hydronium ions combine with the hydroxide ions of the sodium hydroxide to form water. In this conventional process, the electrolyte is thus converted to weakly ionized form to accomplish suppression. During this process, the exchangeable hydrogen ions are depleted and replaced with sodium ions. Thereafter, the effluent from the suppressor is directed through conductivity cell 168 in which the separated anions are detected and from there to waste.

After completion of the analytical run (i.e., after chromatographic separation, suppression and detection), an electrical potential is applied through the resin in the packed bed suppressor while flowing an aqueous liquid stream to electrolyze water in the stream. Hydronium ions generated at the anode displace the sodium ions which associate with the hydroxide ions for passage to waste, in this instance through the conductivity cell.

Typical conditions for regeneration include current applied at a voltage of 3 VDC to 50 VDC and preferably 5 VDC to 15 VDC and a current of 20 mA to 1000 mA and preferably 100 mA to 500 mA for a short period of time, suitably up to about 1 to 10 minutes and preferably on the order of 1 to 5 minutes while the aqueous liquid stream is flowing (e.g. at a rate of 1 mL/min) through the suppressor to provide the source of hydronium ions. In one embodiment, the source of hydronium ion is the eluent from reservoir 150 without any sample. Since the eluent includes sodium hydroxide, the current applied must produce sufficient hydronium ions to shift the equilibrium toward the hydrogen ion form of the ion exchange resin in the suppressor.

After regeneration, the power supply 164 is discontinued and the aqueous liquid stream permitted to flow through the suppressor for sufficient time for equilibration, typically 1 to 5 minutes. This allows generated gas bubbles to sweep out of the bed and the settling of the conductivity cell and the baseline. Thereafter, a new sample is injected for subsequent detection. Since the eluent contains sodium ions, removal efficiency of sodium ions from the ion exchange sites is significantly reduced during regeneration. The sodium ions compete with the hydronium ions that are generated at the anode which can make it difficult to remove sodium ions. In certain instances, this can result in peak area variation as time proceeds as well as incomplete suppression of the analyte.

Figure 2:
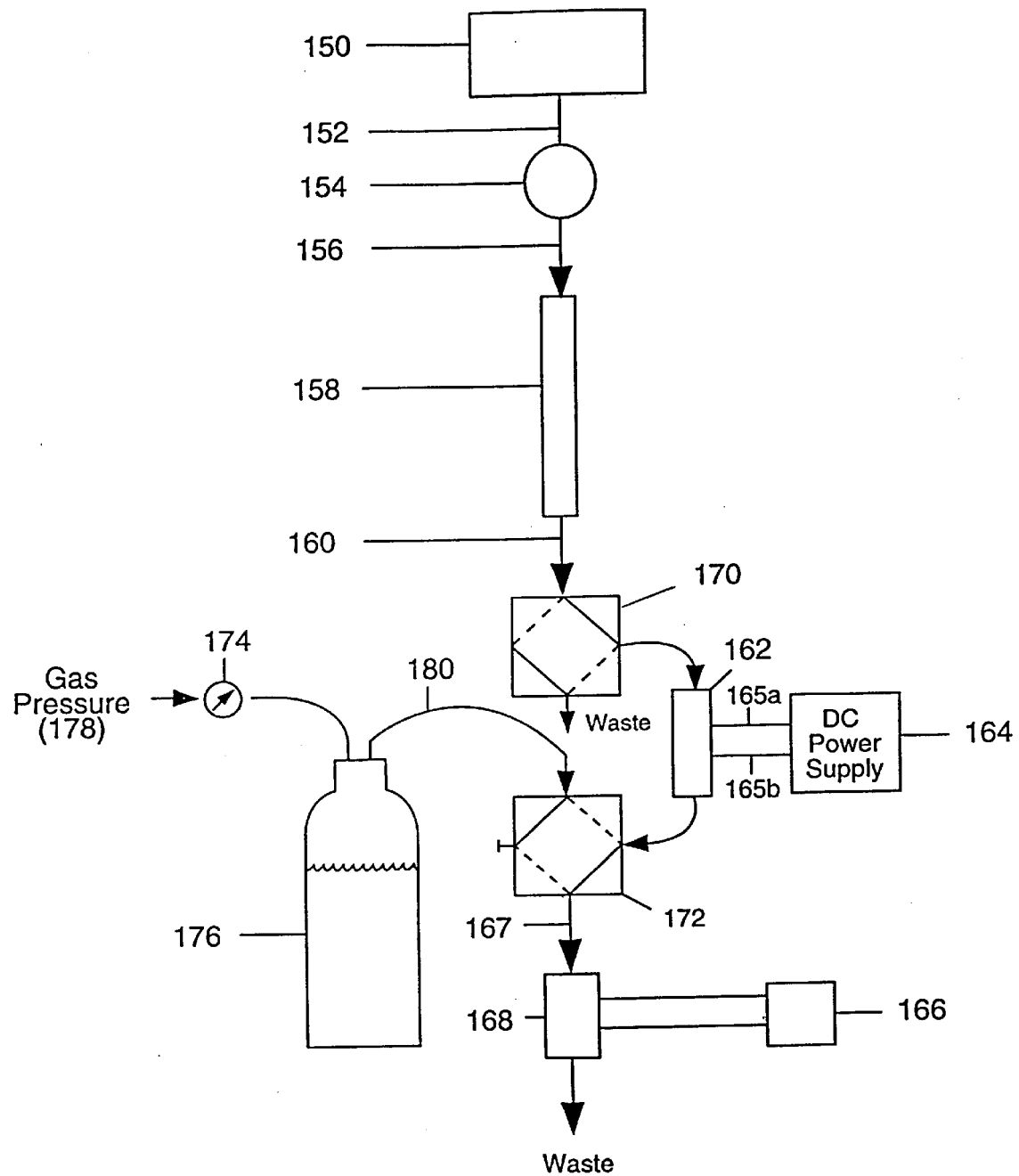

To overcome the foregoing potential problem, a source of water, preferably deionized water, may be directed through the suppressor during regeneration. FIG. 2 illustrates a system for supplying deionized water to the suppressor during regeneration. Similar parts will be designated with similar numbers for FIGS. 1 and 2. Three-way slider valves 170 and 172 may be used for the proper shifting between the flow of deionized water and eluent. Deionized water is supplied by reservoir 176 under control of pressurized gas from source 178 through line 180 to valve 172.

FIG. 2 illustrates the analytical run setting for valves 170 and 172. Specifically, the chromatography effluent from column 158 passes through tubing 160 to valve 170 through suppressor 162, valve 172, tubing 164, conductivity cell 168, and to waste. After completion of the run, the settings of valves 170 and 172 are reversed so that the deionized water in tank 176 passes through line 180, valve 172, suppressor 162, valve 170 and to waste. In this particular embodiment, the flow through the suppressor is reversed for suppression and regeneration. Other valving arrangements may be employed including one in which the flow is in the same direction so long as the deionized water and eluent are independently directed through the suppressor.

By use of deionized water, more complete regeneration can be accomplished in a shorter time and with a lower voltage current supply. For example, a suitable time for regeneration is on the order of 0.5 min to 5 min using a flowrate of 1 mL/min, a voltage of about 5 VDC to about 15 VDC, and a current of about 100 mA to 1000 mA.

Many different forms of electrolytic chemical suppressors may be employed in accordance with the present invention. High capacity (e.g., 2 to 10 mEq/g) resin conventionally used for ion chromatography suppressors is packed into a column. The operation of the column as a suppressor and its configuration can be similar to that of a conventional packed bed suppressor such as set forth in the aforementioned U.S. patents (U.S. Pat. Nos. 3,897,213; 3,920,397; 3,925,019; and 3,926,559). An important feature of the suppressor is the use of means for applying an electrical potential across the ion exchange resin. Any number of configurations may be employed so long as the potential is applied to a significant part of the resin for efficient regeneration. In that regard, the anode and cathode should be spaced apart with the majority of the ion exchange resin disposed therebetween.

Figures 3, 3A:
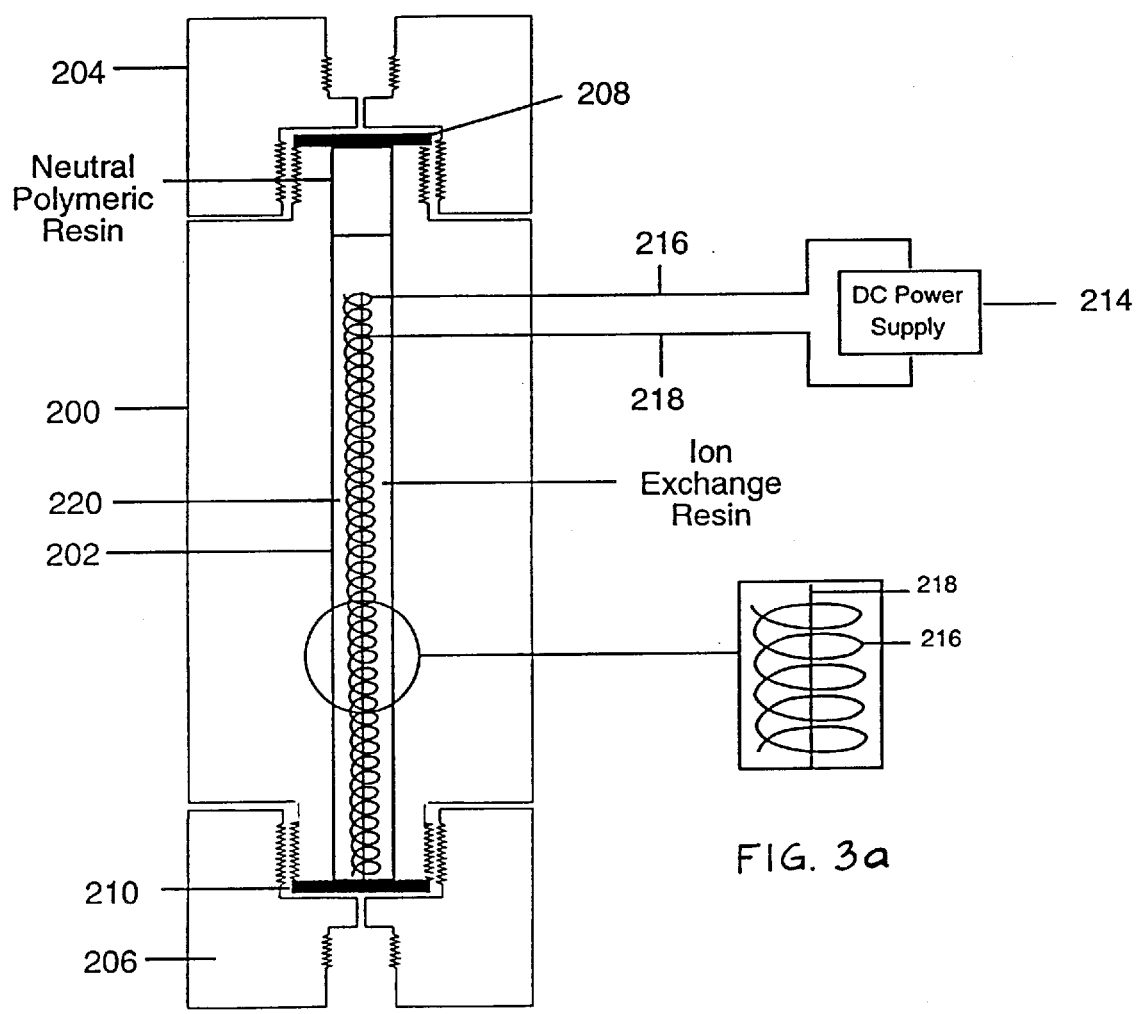
FIGS. 3 and 3a are embodiments of an electrolytic chemical packed bed suppressor according to the invention in cross-section and expanded partially broken away views.

One embodiment of a suitable suppressor is illustrated in FIG. 3. The flowthrough housing (suitably in cylindrical cross-section) includes a body 200 with a central bore 202, screw-threaded top and bottom end caps 204 and 206, and top and bottom flow-through bed supports 208 and 210, respectively, at opposite ends of bore 202. A DC power supply 214 is connected to a cathode 216 and an anode 218. In this instance, the anode is formed into a helical spiral which extends along the length of bore 202. Cathode 216 coaxially projects in a generally straight line along the axis of the circular bore. The cathode and anode are suitably formed of platinum. High capacity ion exchange resin 220 is filled into bore 202 with cathode 216 and anode 218 in place. Above the top of the ion exchange resin bed and the electrodes is a small bed of neutral resin (e.g. formed of crosslinked polystyrene) or other porous neutral packing material. It serves the function of taking up the excess volume between the liquid connection to the suppressor column and the electrode which would otherwise be a source of band dispersion. Bed supports 208 and 210 are positioned and end caps 204 and 206 are screwed into a secured position. As is conventional, end caps include screw-threaded ports for connection to the inlet and outlet tubing.

FIG. 3a illustrates an exploded view partially broken away of the configuration of anode and cathode in contact in the ion exchange resin bed.

Another embodiment of suitable electrolytic chemical suppressor is illustrated in FIG. 4. Like parts will be designated with like numbers for FIGS. 3 and 4. In this instance, the DC power supply is connected to spaced cathode 216 and anode 218 separated by non-conducting spacers 224 and projecting from the top to the bottom of the suppressor along the ion exchange resin in direct contact with the resin. This is best illustrated in FIGS. 4a, a cross-sectional view along the line AA of FIG. 4. The facing generally C-shaped cathode 216 and anode 218 project substantially along the entire length of ion exchange resin 220 in bore 202. At the top and bottom of the ion exchange resin bed are small beds of neutral polymeric resin 230 and 232, respectively. The reason for this neutral polymeric resin is the same as with respect to the embodiment of FIG. 15, namely to take up excess volume and prevent peak dispersion.

Figure 5:
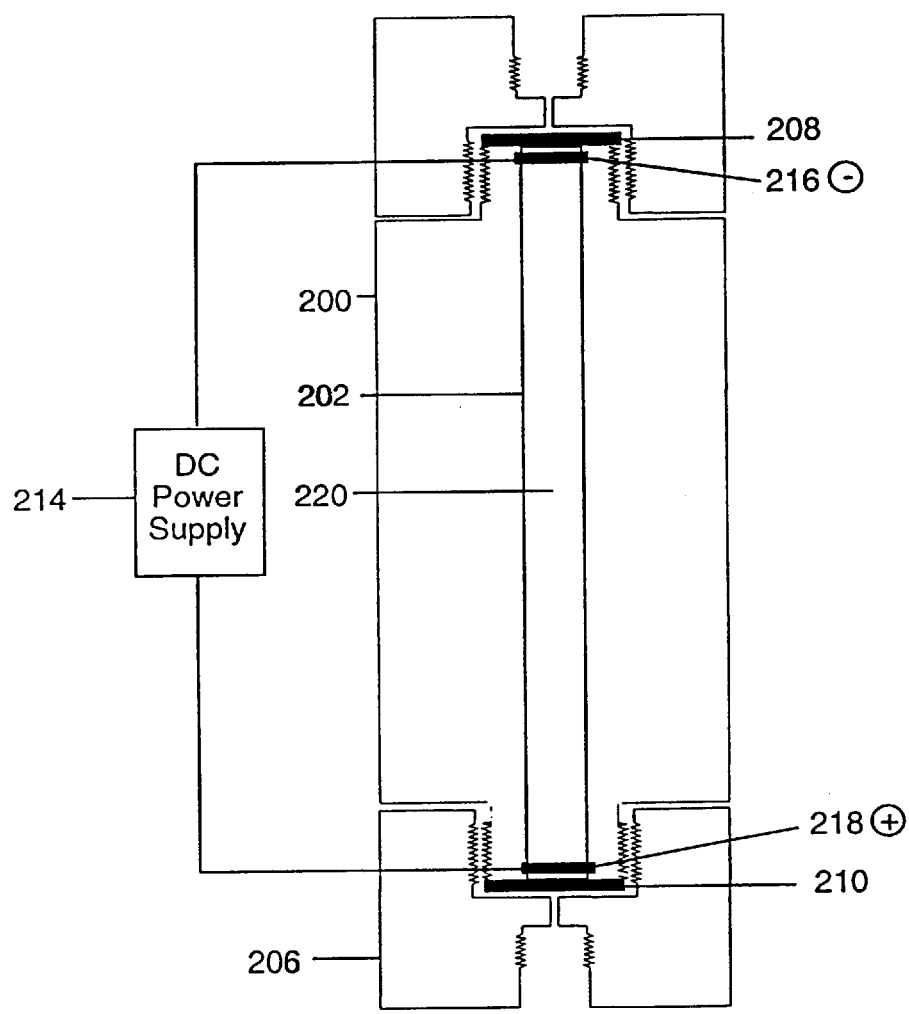
FIG. 5 is a cross-sectional view of another electrolytic chemical suppressor.

Another embodiment of a suitable electrolytic chemical suppressor is illustrated in FIG. 5. Like parts will be designated with like numbers to that of FIG. 3. The main differences among the embodiments of FIGS. 3, 4, and 5 are the location, configuration and disposition of the anode and cathode. In FIG. 5, the anode and cathode are at the top and bottom of the ion exchange resin beds. The anode and cathode are formed, for example, from a screen mesh or porous disc of platinum so as to allow liquid flow through the electrode and are placed directly on the top and bottom of the resin bed in direct contact with the resin.

In the case of screen mesh, a disc of porous polyethylene is also used outside the electrode as a resin bed support to hold the resin on the column. The cross section of the suppressor bed in this embodiment need not be circular. Square and rectangular cross sections with appropriate geometry electrodes placed at opposite ends of the resin bed are other embodiments of this design.

The embodiment of FIG. 5 can have certain advantages. Since the electrodes are placed at the entry and exit ports of the column, this design efficiently removes sodium ions from the ion exchange sites because the suppressor generates hydronium ion at the entry in the flow direction, which allows these ions to displace sodium ions on the bed. Sodium ions can then exit the suppressor by association with hydroxide ions so they are generated at the exit port.

However, by placing the electrodes at the opposite ends of the ion exchange resin beds, flow preferably is counter-current to the flow of column effluent because it is best to generate the suppression ions (and thus conversion of the ion exchange sites) at the outlet end so that the bed is substantially regenerated for analysis. This prevents the counter-ions to the analyte from converting to the hydronium ion when entering the bed and then converting again to the sodium form upon exiting.

Figure 6:
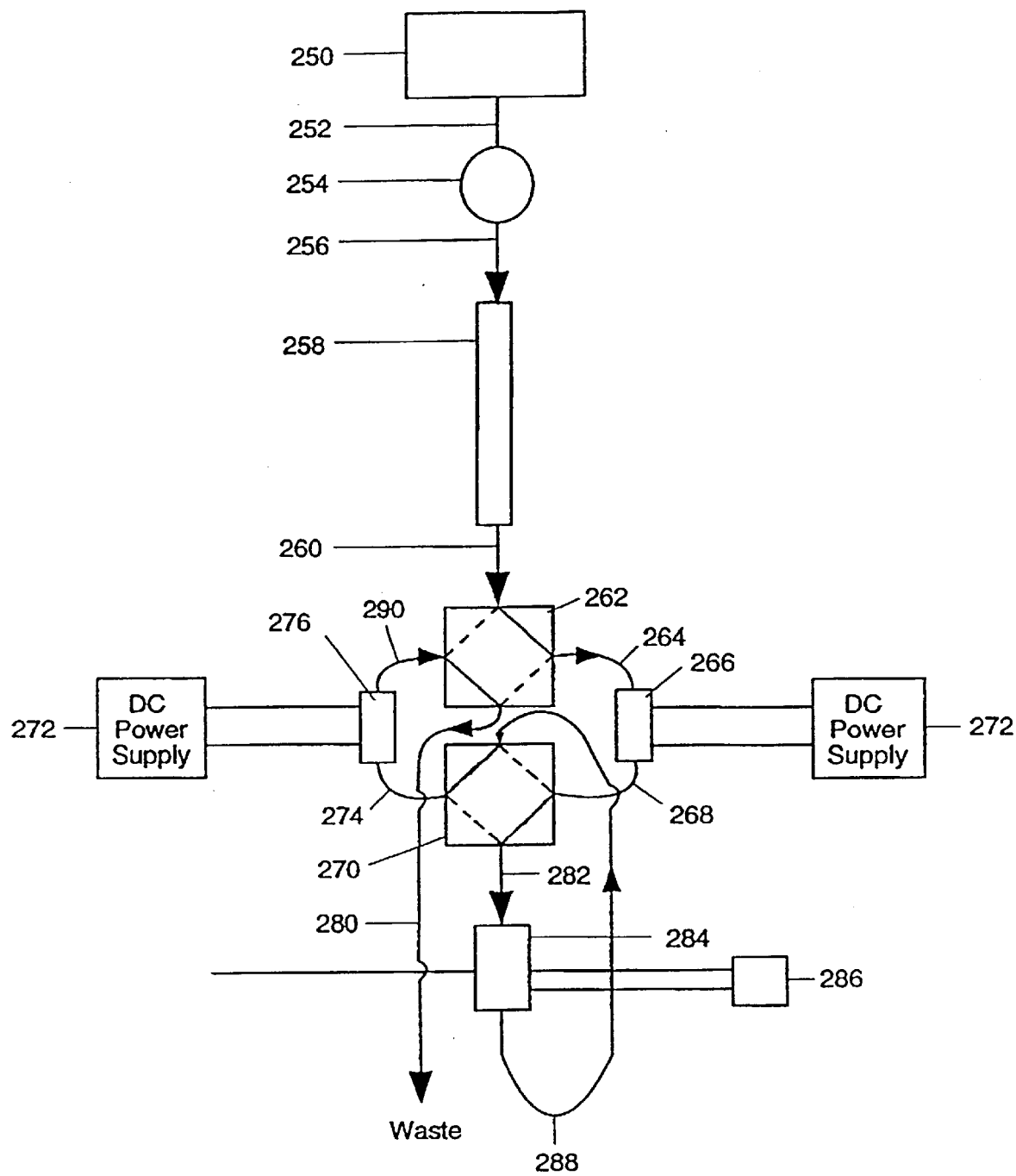
FIG. 6 is a schematic view of a system according to the invention using two ion exchange packed beds, one used as a suppressor and the other as either a suppressor or polishing unit.

Referring to FIG. 6, a form of the invention is illustrated which includes two electrolytic packed bed units. In one instance, only one of the ion exchange packed beds is used as a suppressor and the other one is used as a polishing unit. In the other system, both ion exchange packed beds are used as suppressors so that analyte is analyzed in one of the suppressors while the other one is being regenerated and then the system can be reversed. The setup of FIG. 6 can be employed for either mode of operation.

Referring to FIG. 6, an analytical pump 250 is connected by tubing 252 to sample injection valve 254, tubing 256 to analytical column 258, and then via tubing 260 to valve 262. One port of valve 262 is connected by tubing 264 to one end of suppressor 266. The other end of suppressor 266 is connected by tubing 268 to valve 270. A DC power supply 272 is connected to suppressor 266 in the manner set forth above. Valve 262 also includes a port connected by tubing 274 to suppressor 276 which, in turn, is also coupled to valve 262 by tubing 290 and to DC power supply 272, also as set forth above. Valve 262 includes a third port connected by line 280 to waste.

Valve 270 includes one port connected to tubing 268, and another port connected by tubing 282 to conductivity cell 284 of conductivity detector 286. Conductivity cell 284 is, in turn, connected by line 288 to another port of valve 270. Valve 270 includes another port connected by tubing 290 to one end of suppressor 276.

Referring to FIG. 5, operation of a system in which both packed beds 266 and 276 are used for suppression is as follows. A sodium chloride analyte is eluted with a sodium hydroxide eluent or any other suitable eluent (e.g., sodium carbonate/bicarbonate). In the analytical stage, analytical pump 250 carries the eluent through line 252 and sample injected through valve 254 is carried in tubing 256 through chromatographic column 258 where the ionic species are separated. The effluent from column 258 is directed through tubing 260 to valve 262 and then through tubing 274 to previously regenerated suppressor 276 (with power from source 278 off). The effluent from suppressor 276 is directed through tubing 290 to valve 270, tubing 288 to conductivity cell 284 where the ionic species are detected. The effluent from conductivity cell 284, typically a weak acid (e.g. in water or carbonic acid), is directed in tubing 282 back through valve 270 through tubing 268 to suppressor 266 with the power supply 272 turned on. In this stage, the ion exchange resin in suppressor 266 is regenerated and the flow of effluent from this suppressor, including the electrolyte (e.g. sodium hydroxide), flows through tubing 264 back through valve 262 and through tubing 280 to waste.

After completion of an analytical run (including separation, suppression and detection) and adequate regeneration of suppressor 266 from a previous analytical run, valves 262 and 270 are reset so that suppressor 266 is on-line for suppression prior to detection and suppressor 276 is regenerated. With a new setting of the valves, the flow proceeds as follows. A new sample is injected through valve 254 and is carried by the eluent from analytical pump 250 through tubing 256, chromatographic column 258, valve 262 and through suppressor 266. During this time, DC power supply 272 is in the off position. After suppression of the eluent, the suppressor effluent flows through tubing 268, valve 270 to conductivity cell 284 in which the ionic species of the second sample are detected. The conductivity cell effluent flows in tubing 282 back to valve 284 and through tubing 290 and then through suppressor 276. In this instance, the conductivity cell effluent serves as the aqueous liquid stream supplying water for electrolysis by the application of current from DC power supply 278 to regenerate the ion exchange resin in suppressor 276. The effluent from suppressor 276 flows through tubing 274, valve 262 and to waste.

In the above system, one suppressor is functional to suppress eluent electrolyte after separation and prior to detection, with power applied, while the other suppressor is off-line and being regenerated with power applied. Then the system is reversed.

Valve means in the form of valves 262 and 270 have first and second valve positions. In the first valve position liquid flows from the eluent reservoir through analytical pump 250, chromatographic separation column 258, suppressor 276, conductivity cell 284 to suppressor 266. In the second valve position, the eluent flows through analytical pump 250, sample injection valve 254, suppressor 266, detector 270, and suppressor 276. In the first valve position the ions in the sample solution are separated in column 258 and carried in the eluent through suppressor 276 in which the electrolyte is converted to weakly ionized form during suppression, and through conductivity cell 284 in which the ions are detected and through suppressor 266. In the second valve position, the eluent solution flows through suppressor 266 and then through suppressor 276.

In another embodiment, the suppressor 266 is used solely as a polishing column to deliver water with low ion concentration to the other suppressor for effective suppression. An advantage of this system is that only a single bed is used for analysis. This eliminates possible changes in peak responses due to differences in geometry which cause differences in dispersion in each suppressor. This may not be significant if the beds can be well matched. One disadvantage of this polishing technique compared to the foregoing polishing technique is that it takes longer for the full run including regeneration.

The polishing system operates in a similar manner. In the first valve setting described above, the system operates identically for either the dual suppressor system or the suppressor/polishing unit system. In particular, the above description applies in which suppressor 276 is on-line as a suppressor after separation and before detection while suppressor 266 is being regenerated. The second valve setting is also the same, with the principal difference that no sample is injected during this cycle. Instead, in the second valve setting, suppressor 276 is regenerated and no readings are taken by conductivity detector 286. Thus, as in the above second valve setting, power supply 278 is on to regenerate suppressor 276 and power supply 272 is off with no analytical function being performed by suppressor 266. Instead, it serves solely as a polish column to supply water of low ionic content to suppressor 276 during the regeneration mode.

In either the dual suppressor mode or suppressor/polisher mode, suppression is performed in accordance with the conditions well known in the art for packed bed suppression for example as illustrated U.S. Pat. Nos. 3,897,213, 3,920, 397, 3,925,019 and 3,926,559.

The conditions for regeneration are similar to those set forth with respect to the system of FIG. 1.

In order to illustrate the present invention, the following examples of its practice are provided.

EXAMPLE 1

This example illustrates the use of an electrolytic chemical packed bed suppressor of the type illustrated in FIG. 3. The unit includes a 4×50 mm column. A length of 0.5 mm platinum wire is coiled in a helical spring-like configuration with the outer diameter of the coil about 4 mm and the coil extending approximately the entire length of the suppressor bed. The second electrode is a straight length of 0.5 mm platinum wire extending the entire length of the column coaxial to the coil. Both of the electrodes exit from the coil through fittings that provide liquid tight seal and make contact with the power supply. The electrode separation is about 2 mm.

The resin was first converted to the exhausted (sodium ion) form with sodium hydroxide, then, with eluent flowing at 2 mL/min, a voltage of 9 volts was applied using the outer coil electrode as the anode. About 500 mA current was obtained, accompanied by visible gassing. The effluent was basic. These observations were compatible with regeneration. The current was applied for 5 minutes, then shut off. Conductivity of the effluent decreased rapidly in the period of about one minute from a reading from about 1000 $\mu$S to about 600 $\mu$S. This indicated that the hydronium ion had been injected electrochemically into the suppressor bed. A 7-anion standard was run:

| | |
|---|---|
| Column: | AS4A SC |
| Flow rate: | 2 mL/min |
| Eluent: | 1.8 mM $Na_2CO_3$/1.7 mM $NaHCO_3$ |
| Injection volume: | 25 $\mu$L |
| 2 ppm $F^-$ | 15 ppm $NO_3^-$ |
| 3 ppm $Cl^-$ | 15 ppm $PO_4^{3-}$ |
| 1 ppm $NO_2^-$ | 15 ppm $SO_4^{2-}$ |
| 10 ppm $Br^-$ | |

Figure 7:
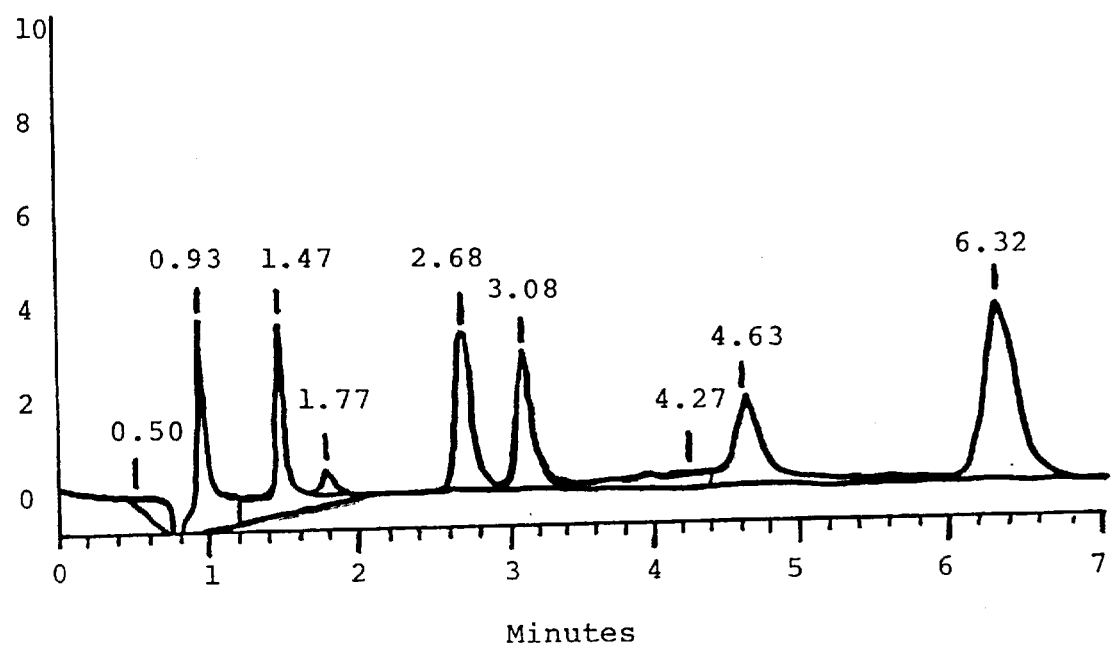
Figure 6:
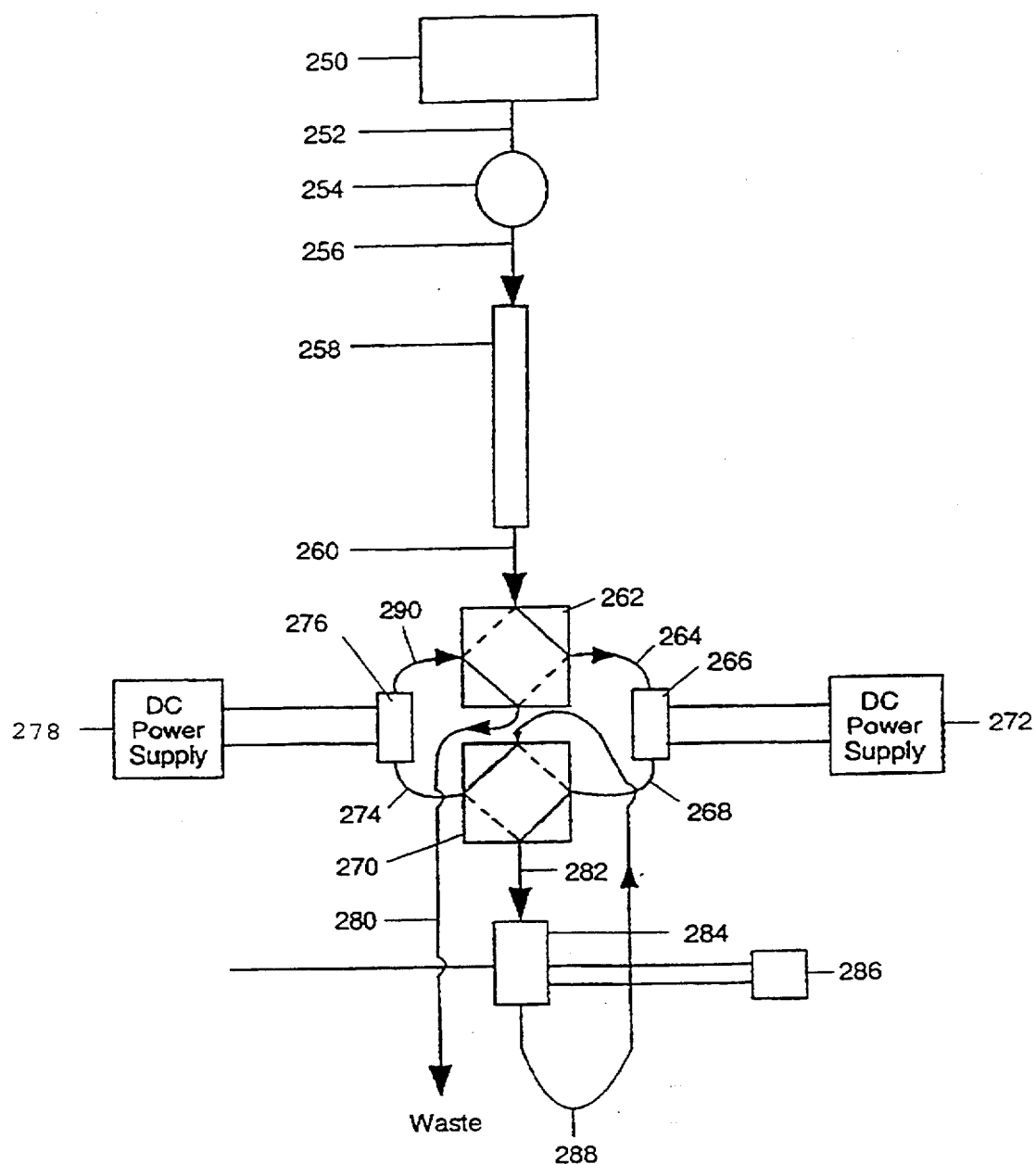

The suppressor was then regenerated at 500 mA for a further 2 minutes and allowed to equilibrate for about 1 minute after stopping the current. The chromatograph of FIG. 7 was obtained illustrating regeneration.

EXAMPLE 2

This example illustrates the use of an electrolytic chemical packed bed suppressor of the type illustrated in FIG. 5.

The unit includes a 6×20 mm column. Porous electrodes were fabricated from platinum mesh and placed at either end of the resin bed. Both of the electrodes were connected to the power supply by wires through fittings in the body of the column that provide a liquid tight seal and make contact with the power supply.

Dowex 50W-X8 resin was first converted to the exhausted (sodium ion) form with sodium hydroxide. An external source of deionized water was supplied as shown in FIG. 2. A voltage of 13 volts was applied from a DC power supply while deionized water was pneumatically pumped through the ion exchange bed at a flow rate of 0.3 mL/minute in the direction from the anode to the cathode (from bottom to top). Thus, sodium hydroxide formed at the cathode was swept from the bed along with the hydrogen and oxygen gases formed at the electrodes. The potential of 13 volts was maintained for 7.5 minutes and the deionized water flow maintained for a further 0.5 minutes. The suppressor was then connected by switching valves 170 and 174 to the exit of the separator column such that the cathode end was attached to the outlet of the separator column and the anode end was attached to the conductivity cell.

The chromatographic system with eluent flowing was allowed to equilibrate for 2.5 minutes. During this time the conductivity of the effluent dropped from 470 $\mu$S to 16 $\mu$S. The sample was injected and the chromatogram shown in FIG. 8 was obtained.

| Column: | AS4A SC |
|---|---|
| Flow rate: | 2 mL/min |
| Eluent: | 1.8 mM $Na_2CO_3$/1.7 mM $NaHCO_3$ |
| Injection volume: | 20 $\mu$L |
| 2 ppm $F^-$ | 10 ppm $NO_3^-$ |
| 3 ppm $Cl^-$ | 15 ppm $PO_4^{3-}$ |
| 15 ppm $SO_4^{2-}$ | |

What is claimed is:

1. A method of anion or cation analysis by ion chromatography using periodic electrolytic chemical regeneration of a packed bed suppressor, said method comprising
   (a) chromatographically separating ionic species in a first liquid sample in a water-containing first eluent solution comprising electrolyte, to form a first chromatography effluent including separated ionic species,
   (b) flowing said first chromatography effluent through a first packed bed suppressor including first suppressor ion exchange resin with first exchangeable ions to convert said electrolyte to weakly ionized form during suppression, thereby depleting at least some of said first exchangeable ions on said first suppressor ion exchange resin, said first chromatography effluent exiting as a first suppressor effluent,
   (c) flowing the first suppressor effluent including the separated ionic species from said first packed bed suppressor through a first detector in which the separated ionic species are detected to form a detector effluent, and
   (d) applying an electrical potential through said first packed resin bed suppressor while flowing an aqueous liquid stream therethrough to electrolyze water in said aqueous liquid stream and thereby regenerate the first exchangeable ions on said first suppressor ion exchange resin, the application of said electrical potential being discontinued during steps (a), (b) and (c).

2. The method of claim 1 in which the ionic species are anions and in which in step (d) water in said aqueous liquid in said first packed bed suppressor is electrolyzed to generate hydronium ions for regeneration of said first exchangeable ions.

3. The method of claim 1 in which the ionic species are cations and in which in step (d) water in said aqueous liquid in said first packed bed suppressor is electrolyzed to generate hydroxide ions for regeneration of said first exchangeable ions.

4. The method of claim 1 further comprising:
   (e) flowing a second water-containing eluent solution comprising electrolyte through a flow-through polishing unit comprising ion exchange resin having exchangeable ions to convert said electrolyte into weakly ionized form and to form a polished liquid effluent, and
   (f) flowing said polished liquid effluent through said first packed bed suppressor during step (d), said polished effluent comprising said aqueous liquid stream.

5. The method of claim 1 in which said aqueous liquid stream comprises a second water-containing eluent solution.

6. The method of claim 1 in which said aqueous liquid stream is supplied from a source of water independent of said eluent solution.

7. The method of claim 6 in which said water from said source independent of said eluent solution is deionized water.

8. Apparatus for analysis of ions in a liquid sample solution comprising
   (a) a reservoir for a water-containing eluent solution comprising electrolyte,
   (b) chromatographic separating means in communication with said eluent reservoir for receiving eluent therefrom, said chromatographic separating means comprising a chromatographic separating medium adapted to separate ionic species of a sample eluted therethrough using said eluent solution,
   (c) means for injecting a liquid sample into said chromatographic separation means,
   (d) a suppressor comprising an ion exchange resin bed in communication with said chromatographic separating means,
   (e) means for applying an electrical potential through said first suppressor ion exchange resin bed to electrolyze water and regenerate said suppressor ion exchange resin, and
   (f) a detector in communication with said suppressor.

9. Apparatus for analysis of ions in a liquid sample solution comprising
   (a) a first reservoir for a water-containing eluent solution comprising electrolyte,
   (b) chromatographic separating means in communication with said eluent reservoir for receiving eluent therefrom, said chromatographic separating means comprising a chromatographic separating medium adapted to separate ionic species of a sample eluted therethrough using said eluent solution,
   (c) means for injecting a liquid sample into said chromatographic separation means,
   (d) a suppressor comprising an ion exchange resin bed in communication with said chromatographic separating means,
   (e) a detector in communication with said suppressor,
   (f) a second reservoir of water in communication with said suppressor,
   (g) means for applying an electrical potential through said suppressor ion exchange resin bed to electrolyze water in a flowing aqueous stream and regenerate said suppressor ion exchange, and (h) valve means including a first and second valve position, said first valve position permitting liquid flow from said first reservoir, through said chromatographic separation means, suppressor, and said detector, and said second position permitting liquid flow from said second reservoir, through said suppressor, whereby in said first valve position, the ions in a sample solution are separated in said chromatographic separating means and carried in said eluent through said suppressor in which said electrolyte is converted to weakly dissociated form during suppression, and through said detector in which the ions are detected, and in said second valve position, water from said second reservoir flows at least through suppressor, said applying means being capable of applying said electrical potential across said suppressor ion exchange resin bed to regenerate said suppressor ion exchange resin bed with said valve means in said second valve position.

10. A method of anion or cation analysis by ion chromatography using periodic electrolytic chemical regeneration of a packed bed suppressor, said method comprising (a) chromatographically separating ionic species in a first liquid sample a water-containing first eluent solution comprising electrolyte, to form a first chromatography effluent including separated ionic species, (b) flowing said first chromatography effluent through a first packed bed suppressor including first suppressor ion exchange resin with first exchangeable ions to convert said electrolyte to weakly ionized form during suppression, thereby depleting at least some of said first exchangeable ions on said first suppressor ion exchange resin, said first chromatography effluent exiting as a first suppressor effluent, (c) flowing the first suppressor effluent including the separated ionic species from said first packed bed suppressor through a first detector in which the separated ionic species are detected to form a detector effluent, (d) applying an electrical potential through said first packed resin bed suppressor while flowing an aqueous liquid stream therethrough to electrolyze water in said aqueous liquid stream and thereby regenerate the first exchangeable ions on said first suppressor ion exchange resin, the application of said electrical potential being discontinued during steps (a), (b) and (c), (e) flowing a second water-containing eluent solution comprising electrolyte through a flow-through polishing unit comprising ion exchange resin having exchangeable ions to convert said electrolyte into weakly ionized form and to form a polished liquid effluent, and (f) flowing said polished liquid effluent through said first packed bed suppressor during step (d), said polished effluent comprising said aqueous liquid stream.

11. The method of claim 10 further comprising the steps of (g) regenerating the ion exchange resin in said polishing column by flowing the effluent from said first detector in step (c) through said polishing unit and applying an electrical potential through said polishing column ion exchange resin to regenerate the exchangeable ions thereon.

* * * * *

UNITED STATES PATENT AND TRADEMARK OFFICE
CERTIFICATE OF CORRECTION

PATENT NO : 5,773,615
DATED : June 30, 1998
INVENTOR(S) : SMALL et al.

It is certified that error appears in the above-identified patent and that said Letters Patent is hereby corrected as shown below:

In Figure 6:
Renumber the DC Power Supply connected to Suppressor (276) by deleting "272" and insert therefore -278-. A corrected Figure 6 is also enclosed.

Column 6, line 56, after "tubing," delete "164" and insert therefore -167-;
Column 8, line 48, after "Valve," delete "262" and insert therefore -270-;
Column 8, line 50, after "power supply," delete "272" and insert therefore -278-;
Column 8, line 57, after "tubing," delete "290" and insert therefore -274-;
Column 8, line 59, after "Fig.," delete "5" and insert therefore -6-;
Column 9, line 1, after "through tubing," delete "274" and insert therefore -290-;
Column 9, line 4, after "through tubing," delete "290" and insert therefore -274-;
Column 9, line 4, after "tubing," delete "288" and insert therefore -282-;
Column 9, line 7, after "tubing," delete "282" and insert therefore -288-;
Column 9, line 27, after "tubing," delete "282" and insert therefore -288-;
Column 9, line 27, after "valve," delete "284" and insert therefore -270-;
Column 9, line 28, after "tubing," delete "290" and insert therefore -274-;
Column 9, line 33, after "through tubing," delete "274" and insert therefore -290-;
Column 9, line 46, delete "detector" and insert therefore -valve-.

Signed and Sealed this

Thirteenth Day of February, 2001

Attest:

NICHOLAS P. GODICI

*Attesting Officer*   *Acting Director of the United States Patent and Trademark Office*